United States Patent [19]

Isaacson et al.

[11] 4,443,759

[45] Apr. 17, 1984

[54] MAGNETIZING CURRENT SUPPLY FOR MAGNETIC PARTICLE INSPECTION WITH SCR'S CONNECTED TO THREE-PHASE SECONDARY WINDINGS FOR RECTIFICATION AND CONTROL

[75] Inventors: Bruce G. Isaacson, Park Ridge; Ralph W. Gruetzmacher, River Grove; Kenneth W. Schroeder, Arlington Heights, all of Ill.

[73] Assignee: Magnaflux Corporation, Chicago, Ill.

[21] Appl. No.: 261,498

[22] Filed: May 7, 1981

[51] Int. Cl.³ .................. G01N 27/82; H02P 13/24; H02M 7/155
[52] U.S. Cl. .................................. 324/216; 324/228; 363/87; 363/129
[58] Field of Search ........ 324/228, 233, 234, 214–216; 323/323, 237, 246, 320; 363/87, 88, 129

[56] References Cited

U.S. PATENT DOCUMENTS

| | | | |
|---|---|---|---|
| 3,134,068 | 5/1964 | Feltman | 363/87 |
| 3,519,913 | 7/1970 | Janecek | 363/129 |
| 3,611,097 | 10/1971 | Joslyn | 363/129 |
| 3,825,812 | 7/1974 | DeBuhr | 363/87 |
| 4,282,569 | 8/1981 | Hardwick et al. | 363/87 |
| 4,348,718 | 9/1982 | Vollrath | 363/87 |
| 4,351,022 | 9/1982 | Dolland et al. | 363/87 |

*Primary Examiner*—Gerard R. Strecker
*Assistant Examiner*—Warren S. Edmonds
*Attorney, Agent, or Firm*—Neuman, Williams, Anderson & Olson

[57] ABSTRACT

Magnetizing current supplies are disclosed for supplying current for magnetizing parts in a magnetic particle inspection system, including SCR's connected in circuit with a three-phase voltage step-down transformer to accurately control the duration and magnitude of magnetizing current. In one type of supply, six SCR's are connected between magnetizing apparatus and terminals of three center tapped secondary windings of a three-phase voltage step-down transformer, the SCR's being operable to rectify current and also being connected to a phase control circuit which controls firing times of all SCR's to control the magnitude of the magnetizing current.

12 Claims, 11 Drawing Figures

MAGNETIZING CURRENT SUPPLY FOR MAGNETIC PARTICLE INSPECTION WITH SCR'S CONNECTED TO THREE-PHASE SECONDARY WINDINGS FOR RECTIFICATION AND CONTROL

This invention relates to a magnetic particle inspection system in which magnetizing current is obtained from a three phase AC supply and more particularly to a system in which SCR's are used and in which magnetizing current is accurately and reliably controlled. The system is highly efficient, is readily and economically manufacturable and is trouble-free in operation.

BACKGROUND OF THE INVENTION

In magnetic particle inspection systems, a part is magnetized prior to or during inspection by passing a current through the part or by passing a current through a coil which surrounds the part, magnetic particles being applied over a surface portion of the part to be concentrated at regions where there are cracks or similar defects. Rectifiers have been generally used to develop a unidirectional magnetizing current from an AC supply, usually with a step-down transformer for developing a high current for passing through the part. Various types of controls have been provided including variable or tapped transformers. More recently, systems using silicon-controlled rectifiers (SCR's) have been used.

In one type of system using SCR's and operative from a single phase supply, a pair of oppositely poled SCR's in series between the single phase supply and a step-down transformer are controlled by controlling the phase angle of firing in relation to a reference phase point or points of the single phase supply. The reference phase points may be established by detecting the crossover points of the single phase voltage. The phase control circuit, in turn, is controlled from a control signal developed in response to a current signal which is proportional to the magnetizing current and a reference signal level which is selected in order to select the output current. The control signal may also be responsive to a voltage signal proportional to the voltage applied to the part, the voltage signal being used to limit the applied voltage until the current through the part reaches a certain level. This type of control has been found to be advantageous in the system designed for single phase operation and for developing relatively low magnetizing currents for the testing of small parts.

For systems for testing of larger parts, three phase supplies have been used and in one type of system, adjustable potentiometers have been used to control the firing angles of SCR's connected in series with the primary windings of a three phase transformer, additional SCR's being provided in the secondary circuit for rectification and polarity control.

SUMMARY OF THE INVENTION

This invention was evolved with the general object of improving the control, operation and reliability of magnetic particle inspection systems while minimizing the positive manufacture, operation and maintenance thereof.

An important aspect of the invention relates to the discovery and recognition of problems with prior systems. One problem relates to difficulties in accurately and rapidly controlling magnetizing current which, it is found, may vary substantially under certain circumstances, particularly as a result of variations in the resistance of a part and variations in the resistance between the part and contact heads engaged therewith. The problem has not been severe with smaller parts and particularly not when using the aforementioned system operative with a single phase supply.

The problem is, however, quite serious when large parts are tested because of the larger required magnetizing currents and the fact that excessive currents can rapidly develop to damage the part and/or rectifiers or other circuit components. For larger parts, three phase supplies are generally required and it is also desirable to be able to operate components at as close as possible to their load-carrying capacities in order to avoid excessive size, weight and cost. In such circumstances, however, a sudden decrease in resistance can easily result in excessive currents which damage components. It is also found that three phase supplies of the magnetic particle inspection system of the prior art cannot be readily controlled to avoid this problem.

Another aspect of the invention is in the discovery and recognition that the type of automatic control as used in the aforementioned single phase system can be used in a three phase system and so connected and operated as to obtain high accurate and reliable control.

In a system constructed in accordance with the invention, three power modules are provided, each of which has SCR's associated therewith. Such power modules are connected between windings of three phase transformer means, and either three phase input lines or the magnetizing means used to supply magnetizing current to a part. Each of the power modules includes phase control means for controlling the firing or triggering of the SCR's. A control circuit is provided which is responsive to a current signal developed in proportion to the magnetizing current and a selected reference signal and which is connected to all three of the power modules to simultaneously control all three of the phase angle control means thereof. With this comparatively simple arrangement, the magnetizing current can be accurately and reliably controlled. If there should be a change in the resistance presented by the part and connections thereto, it is immediately sensed and the control circuit rapidly responds to control the phase angle of triggering of the three SCR circuits so as to maintain the magnetizing current at the selected value and so as to prevent excessive current.

In accordance with a specific feature of the invention, the power modules are such that the phase angle of triggering is controlled in accordance with the magnitude of an applied control signal and the control signal applied from the control means has a magnitude controlled by comparison of the current and reference signals. Preferably, the phase angle control of each power module is adjustable to obtain the same relationship between the magnitude of the applied control signal and the phase angle of operation of the firing means in all three modules.

In accordance with another specific feature, the current signal is compared with a reference signal for simultaneous control of the three phase angle controls with the reference signal being adjustable in order to set the magnetizing current at any desired value.

A further feature relates to the modification of the control in response to a voltage signal proportional to the voltage applied to the magnetizing means. Preferably, the voltage signal, current signal and reference signal are compared by comparison means and when the current signal reaches a certain level, the control from the voltage signal is inhibited.

In one embodiment, the SCR's are connected between the primary windings of the transformers and the input supply lines, preferably with a delta connection.

In another embodiment, the power modules are connected in the supply lines with the three primary windings being directly connected in a delta configuration.

In a further embodiment, the power module controls are used to control SCR's in the secondary circuit which has an important advantage with respect to the manufacture and operation of the system. The SCR's in this arrangement serve the dual function of both rectifying and controlling the amount of magnetizing current.

This invention contemplates other objects, features and advantages which will become more fully apparent from the following detailed description taken in conjunction with the accompanying drawings.

DESCRIPTION OF A PREFERRED EMBODIMENT

Reference numeral 10 generally designates inspection equipment constructed in accordance with the invention and designed for the inspection of parts using a magnetic particle inspection method. As diagrammatically illustrated in FIG. 1, the equipment includes a headstock 11 and a tailstock 12 which form one type of magnetizing means and which may be conductively engaged with opposite ends of a part for passing current through the part to magnetize the part. Alternatively, a part may be magnetized by placing it in a coil 13 through which current is passed. During or after magnetization, magnetic particles may be applied to the surface of the part to be concentrated over cracks or other defects in the part and to indicate the location and size of the defects.

Figure 1:
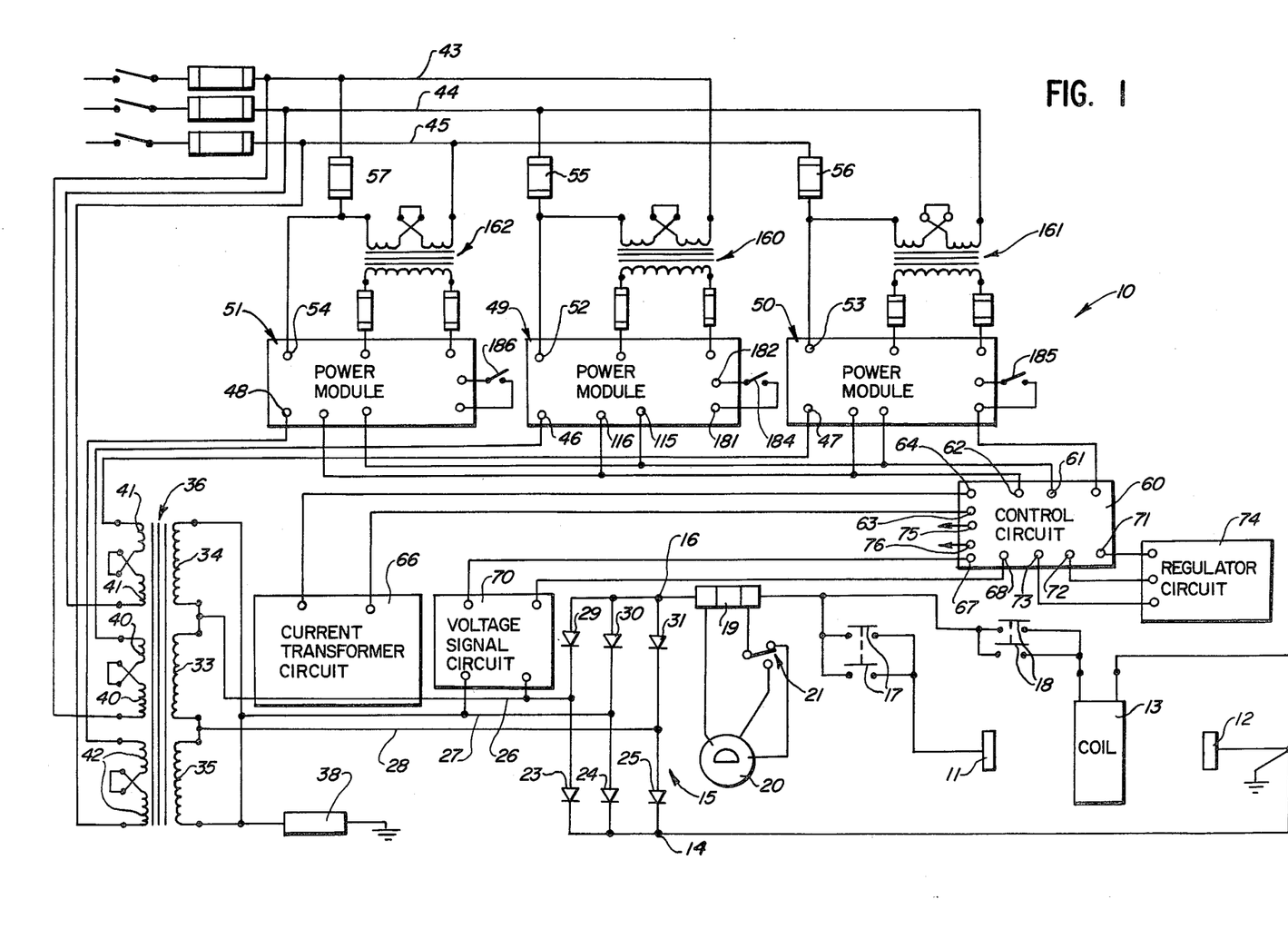
FIG. 1 is a schematic diagram of a magnetic particle inspection system constructed in accordance with the invention.

To apply current to the magnetizing means, the tailstock 12 and one terminal of the coil 13 are connected to output terminal 14 of a rectifier 15 and the headstock 11 and the other terminal of the coil 13 are selectively connectable to a second terminal 16 of the rectifier 15 through selectively operable contacts 17 and 18 and through a shunt 19 which is connected to a meter 20 through a low range-high range selector switch 21.

The rectifier 15 includes diodes 23, 24 and 25 having cathodes connected to the terminal 14 and having anodes connected to lines 26, 27 and 28, and diodes 29, 30 and 31 having anodes connected to the terminal 16 and having cathodes respectively connected to the lines 26, 27 and 28. The lines 26, 27 and 28 are connected to secondary windings 33, 34 and 35 of a three-phase transformer 36, the windings 33, 34 and 35 being connected in a delta fashion with a resistance 38 being connected between line 27 and ground.

The transformer 36 has three sets of primary windings 40, 41 and 42 which may be connected either in parallel or series depending upon the supply voltage, series connections being shown. The windings 40-42 are connected between three-phase power input buses 43, 44 and 45 and terminals 46, 47 and 48 of three power modules 49, 50 and 51. The power modules 49, 50 and 51 have input terminals 52, 53 and 54 which are connected through fuses 55, 56 and 57 to the input buses 44, 45 and 43, respectively. The power modules 49-51, as hereinafter described, include silicon-controlled rectifiers connected between the terminals 46-48 and the terminals 52-54 for completion of current flow paths from buses 43, 44 and 45 and through transformer primary windings 40, 41 and 42 and back to the buses 43, 44 and 45, respectively, a delta configuration of current flow paths being provided.

In accordance with the invention, the phase angle of triggering of the silicon-controlled rectifiers is controlled automatically in a manner such that the three phase system supplies a substantially constant and controllable output current under testing conditions but with limitations on the applied voltage in a manner such as to protect the system and parts being inspected from damage.

The automatic control is effected from a single control circuit 60 which has output terminals 61 and 62 connected to all three of the power modules 49, 50 and 51.

The single control circuit 60 has a pair of input terminals 63 and 64 which are connected to current transformer circuitry generally designated by reference numeral 66, operative to develop an AC signal which is proportional to the current flow in the line 26 between the transformer 36 and the rectifier 15. In addition, the single control circuit 60 has terminals 67 and 68 which are connected to a voltage signal circuit 70. Circuit 70 is connected to the lines 26 and 27 and operates to supply a voltage signal proportional to the voltage between the lines 26 and 27.

The single control circuit 60 further includes terminals 71, 72 and 73 connected to a regulator circuit generally designated by reference numeral 74 and terminals 75 and 76 which are connected to a step-down transformer, not shown, operative to supply an AC supply voltage to the circuit 60.

The circuitry of the control circuit 60 has been used only in control of a single power module such as one of the modules 49-51, and an important aspect of the invention relates to the use of the single control circuit 60 to simultaneously control three power modules to obtain three phase operation. A number of features of the circuitry of the control circuit and the power modules are important to this aspect of the invention.

Figure 2:
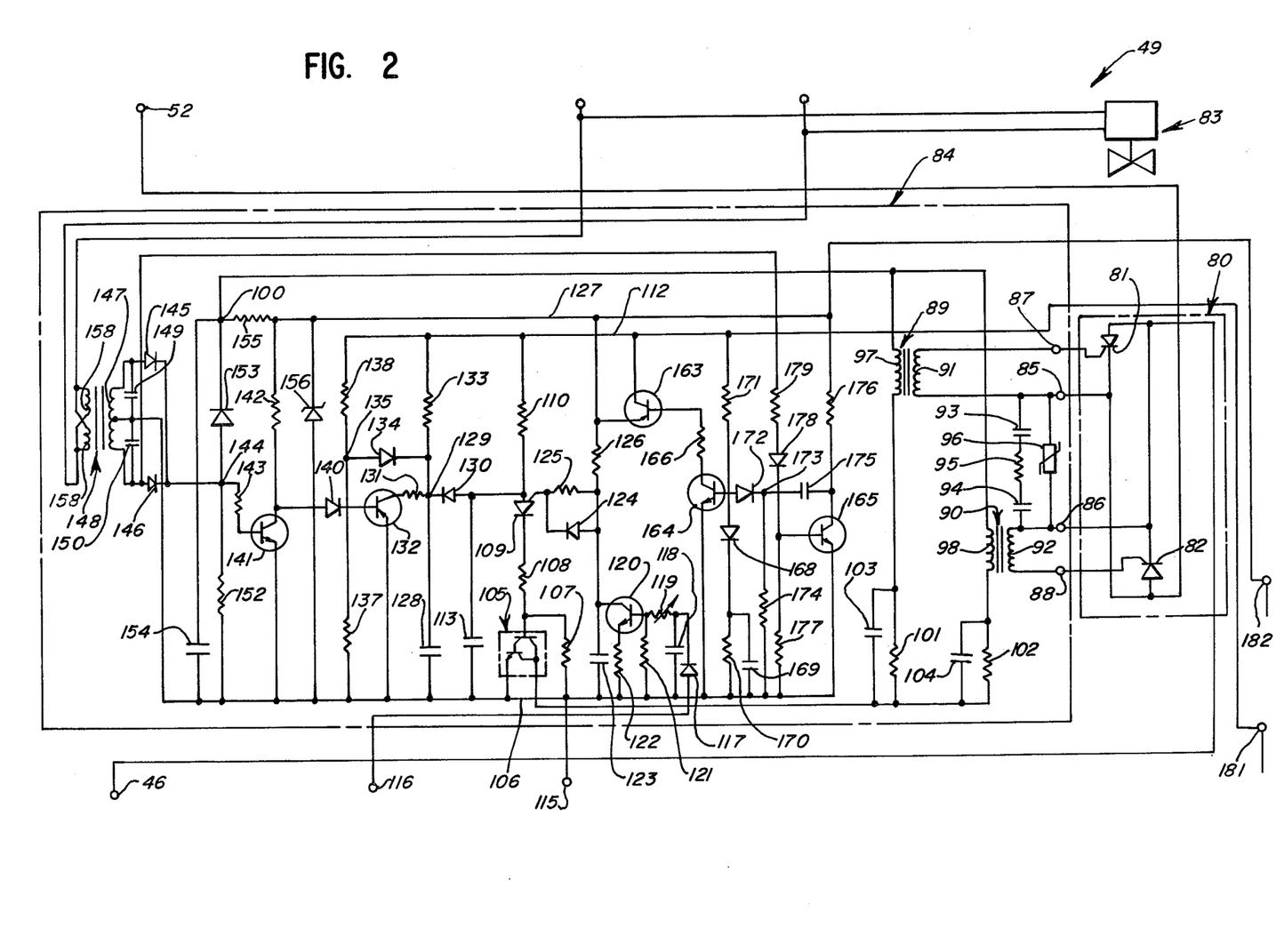
FIG. 2 is a circuit diagram of one of three power modules of the system of FIG. 1.

The circuitry of the power module 49 is shown in FIG. 2 and it will be understood that the power modules 50 and 51 have the same circuitry as the module 49. As shown in FIG. 2, the power module 49 includes a rectifier assembly 80 which includes a pair of silicon-controlled rectifiers 81 and 82 connected to the terminals 46 and 52, the silicon-controlled rectifiers being mounted on a suitable heat sink, not shown, which may be cooled through the use of a suitable fan or blower unit 83 as diagrammatically shown. The power module 49 also includes a printed circuit board 84 which includes terminals 85 and 86 connected to the cathodes of the rectifiers 81 and 82 and terminals 87 and 88 connected to the gate electrodes of the rectifiers 81 and 82. The anode of each of the rectifiers is connected to the anode of the other. Rectifier 81 is operative to conduct current from terminal 46 to terminal 52 and rectifier 82 is operative to conduct current in the reverse direction.

To apply triggering signals to the rectifiers 81 and 82, a pair of transformers 89 and 90 are provided having secondary windings 91 and 92 connected to terminals 85 and 87 and terminals 86 and 88, respectively. A balance network including capacitors 93 and 94, a fixed resistor 95 and a varistor 96 is connected between terminals 85 and 86. The transformers 91 and 92 have primary windings 97 and 98 which are connected to a current point 100 at which a positive supply voltage is applied as hereinafter described.

To develop current pulses in the primary windings 97 and 98, they are also connected through parallel combinations of resistors 101 and 102 and capacitors 103 and 104 to a transistor 105 which is connected to a line 106 forming a reference ground for the circuit. The transistor 105 has an input terminal connected through a resistor 107 to ground and through a resistor 108 to the cathode of a transistor device 109 which operates as a relaxation oscillator and which has an anode connected through a resistor 110 to a line 112 to which a positive DC power supply voltage is applied during operation of the circuit. The anode of the device 109 is also connected through a capacitor 113 to ground and operates as a relaxation oscillator to apply a train of short duration pulses through transistor 105 and transformers 89 and 90 to the gates of the silicon-controlled rectifiers 81 and 82.

The time or phase angle of application of the trains of pulses is controlled in accordance with the magnitude of an input signal applied between input terminals 115 and 116 which are connected through lines 61 and 62 to the control circuit 60. Terminal 115 is connected to the ground line 106 and terminal 116 is connected through a diode 117 and a capacitor 118 to ground, the junction therebetween being connected through an adjustable resistor 119 to the base of a transistor 120 which is connected through a resistor 121 to ground. The emitter of transistor 120 is connected through a resistor 122 to ground and the collector thereof is connected through a capacitor 123 to ground, through a diode 124 and a resistor 125 in parallel to the gate of the device 109 and through a resistor 126 to a line 127 to which a positive DC supply voltage is applied during operation of the circuit.

The transistor 120 operates in response to an increasing magnitude of input voltage at the terminal 116 to lower the potential at the gate electrode of the device 109 and, through a resultant effect on a ramp circuit, to advance the phase of the trains of pulses produced and to thereby increase the duration of time of conduction of the silicon-controlled rectifiers 81 and 82.

The phase control so obtained is achieved through the connection of the anode of the device 109 to a ramp circuit which is triggered at the beginning of each half cycle of an AC supply voltage of one phase which is applied to the power module.

The ramp circuit includes a capacitor 128 which is connected between the ground line 106 and a circuit point 129 which is connected through a diode 130 to the anode of the device 109, through a resistor 131 to the collector of a transistor 132, through a resistor 133 to the line 112 and through a diode 134 to a circuit point 135. The circuit point 135 is connected through a resistor 137 to ground and through a resistor 138 to the line 112.

Figure 3:
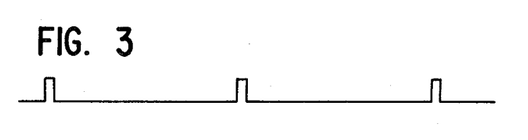
FIGS. 3, 4, 5, 6 and 7 illustrate the waveforms developed at certain points of the circuit of FIG. 2 during a typical operation, for explanation of the operation thereof.

The operation of the ramp circuit will be best understood with reference to FIGS. 3, 4, 5, 6 and 7. In the operation of the ramp circuit, a positive timing pulse is applied to the base of the transistor 132 to render it conductive and to discharge the capacitor 128 as well as the capacitor 113. The form of the pulses applied to the base of the transistor 132 is illustrated in FIG. 3. After each such pulse is applied, the capacitor 128 is charged at a relatively rapid rate through the diode 134 and resistor 138 until a certain level is reached which is determined by the relative values of the resistors 137 and 138. Then the capacitor 128 is charged at a less rapid rate through the resistor 133, then developing a ramp voltage for phase control.

Figure 4:
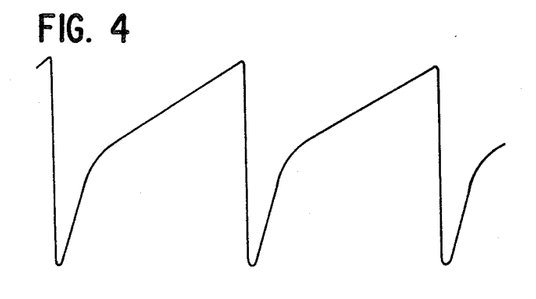

The form of the ramp voltage so developed, as it appears at the collector of the transistor 132, is illustrated in FIG. 4.

Figure 5:
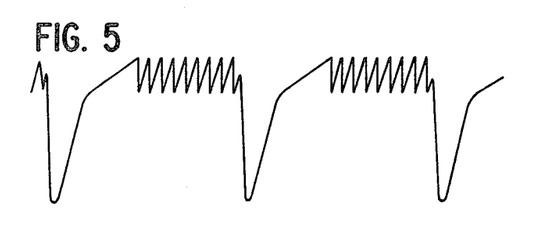
Figure 6:
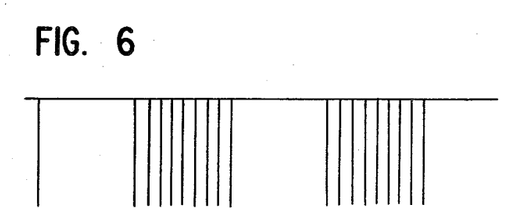
Figure 7:
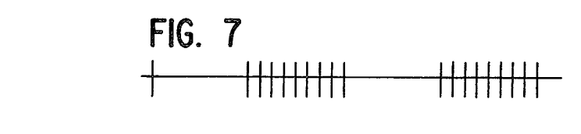

At a certain time in each half cycle, the level of the ramp voltage at the circuit point 129 will reach a value which will allow operation of the relaxation oscillator circuit which includes the transistor 109, resistor 110 and capacitor 113. The time at which such occurs is dependent upon the level of the voltage applied to the gate electrode of the device 109 which, in turn, is dependent upon the input control voltage applied through lines 61 and 62 to the terminals 115 and 116. When the relaxation oscillator action occurs, a sawtooth signal is developed at the anode of the device 109, at a frequency substantially higher than the power frequency. FIG. 5 illustrates the form of the signal developed at the anode of the device 109, under a typical condition. FIG. 6 illustrates the corresponding signal developed by the transistor 105 and applied through the resistors 101 and 102 and capacitors 103 and 104 to the primary windings 97 and 98. FIG. 7 shows the waveform of the corresponding trains of pulses developed at the secondary windings 91 and 92.

The use of a train of pulses for triggering purposes is advantageous in insuring excitation of the gates of the silicon-controlled rectifiers 81 and 82 while minimizing power dissipation.

It is noted that FIGS. 5, 6 and 7 illustrate a typical condition. When the control voltage applied through lines 61 and 62 to terminals 115 and 116 is reduced, the initial pulse of each train will be produced at a later time in each half cycle and the number of pulses in each train will be reduced. Similarly, when the control voltage is increased, the initial triggering pulse occurs at an earlier time and the number of pulses in each train is increased. The relationship between the magnitude of the control voltage and the timing of the initial triggering pulse is accurately adjustable by adjustment of the resistor 119 and the same relationship can be obtained in all three power modules.

To develop timing pulses such as shown in FIG. 3 for control of the ramp circuit, the base of the transistor 132 (FIG. 2) is connected through a diode 140 to the collector of a transistor 141 which is connected through a resistor 142 to the line 127. The base of the transistor 141 is connected through a resistor 143 to a circuit point 144 which forms the output terminal of a full wave rectifier which includes a pair of diodes 145 and 146 connected to end terminals of a secondary winding 147 of a transformer 148, the secondary winding 147 having a center tap connected to the ground line 106 and also connected through capacitors 149 and 150 to the end terminals of the winding 147. The circuit point 144 is at a relatively high potential relative to the potential of the ground line 106 to maintain the transistor 141 conductive except at the crossover points, when the transistor 141 is cut off to develop a positive pulse at its collector. Thus a series of positive pulses are developed at the collector of transistor 141, such being applied through diode 140 to the base of transistor 132. FIG. 3 illustrates the form of the pulses applied to the base of the transistor 132.

Additional power supply circuitry is provided including a resistor 152 between circuit point 144 and ground and a diode 153 between circuit point 144 and circuit point 100 which is connected through a filter capacitor 154 to ground. Circuit point 100 is also connected through a resistor 155 to the line 127 which is connected through a zener diode 156 to ground, to regulate the voltage at the line 127.

To energize transformer 148, it has a primary winding 158 which is connected to the secondary winding of a step-down transformer 160 shown in FIG. 1, the primary winding of transformer 160 being connected to lines 43 and 44. Transformers 161 and 162, similar to the transformer 160 are used to provide supply voltages for the power modules 50 and 51.

The power module of FIG. 2 further includes circuitry to insure that when the conduction of the silicon-controlled rectifiers is terminated, it will always occur at the end of a half cycle of a certain polarity. This is important for half wave operation in which a uniform quick break of current is desirable. To obtain such operation, a latch circuit is provided which includes a pair of transistors 163 and 164 and a reset circuit is provided which includes a transistor 165. The transistor 163 has collector and emitter electrodes connected to the lines 112 and 127, respectively, and a base electrode connected through a resistor 166 to the collector of the transistor 164 which has a grounded emitter. The base of the transistor 164 is connected through a diode 168 and through a capacitor 169 and a resistor 170 in parallel to the ground line 106, also through a resistor 171 to the line 112. The base of the transistor 164 is additionally connected through a diode 172 to a circuit point 173 which is connected through a resistor 174 to ground and through a capacitor 175 to the collector of the transistor 165. The collector of the transistor 165 is connected through a resistor 176 to the line 127 and its base is connected through a resistor 177 to ground and through a diode 178 and a resistor 179 to one end terminal of the transformer secondary winding 147.

Operation of the circuit is initiated by connecting together a pair of terminals 181 and 182 which are connected to the lines 112 and 127. When such lines are connected together, the transistors 164 and 163 of the latch circuit are rendered conductive and the latch circuit is placed in a latched condition to render the circuitry operative as described previously. At the end of each half cycle of one polarity, the latch circuit is reset by a signal applied to the base of the transistor 165, the circuit being again latched during the initial portion of the following half cycle. However, when the terminals 181 and 182 are no longer connected together, the latch circuit will not be again latched after being reset and the operation is always discontinued following a half cycle of a predetermined polarity.

It is noted that terminals 181 and 182 are connected to a relay contact 184, shown in FIG. 1, which is closed in response to operation of a pushbutton or foot switch, not shown. Similar terminals of the modules 50 and 51 are connected to contacts 185 and 186 of the same relay.

Figure 8:
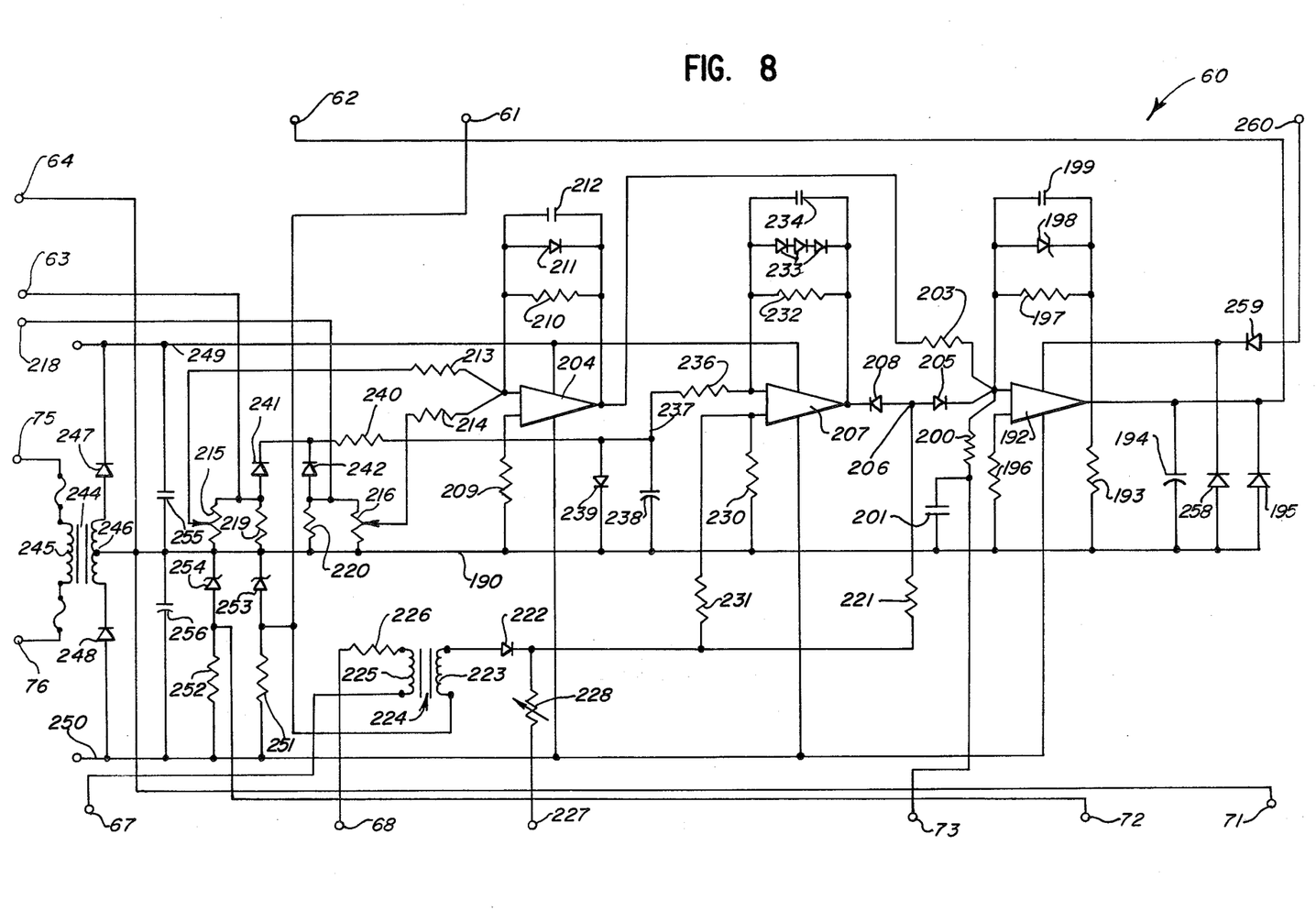
FIG. 8 is a circuit diagram of a control circuit of the system of FIG. 1.

FIG. 8 shows the circuitry of the control circuit 60 which includes the output terminals 61 and 62 connected to the three power modules 49, 50 and 51. The terminal 61 is supplied with a negative bias potential relative to a line 190 which forms a reference ground for the circuit. The terminal 62 is connected to the output of an operational amplifier 192 and also through a resistor 193, a capacitor 194 and a diode 195 to the ground line 190. The operational amplifier 192 has one input connected through a resistor 196 to ground and a second input connected to its output through the parallel combination of a resistor 197, a zener diode 198 and a capacitor 199.

The signal at the second input of the amplifier 192 is controllable from three signals, the first being a reference signal applied through a resistor 200 from the input terminal 73 which is connected to the regulating circuit 74, a capacitor 201 being connected between terminal 73 and the ground line 190.

The second signal applied to the input of the amplifier 192 is a magnetizing current signal applied through a resistor 203 from an amplifier 204. It is proportional to the RMS or average current developed in the output circuit during magnetization of the part.

The third signal is applied through a diode 205 from a circuit point 206 and is a magnetizing voltage signal proportional to the voltage developed in the output circuit when the magnetizing current is initially applied. However, if and when a substantial magnetizing current is developed, the voltage signal developed at circuit point 206 is effectively switched off by means of an amplifier 207 having an output connected through a diode 208 to the circuit point 206.

With regard to the current signal-applying amplifier 204, it has a first input connected through a resistor 209 to ground and a second input connected to its output through the parallel combination of the resistor 210, a diode 211 and a capacitor 212. The second input is connected through resistors 213 and 214 to the movable contacts of two potentiometers 215 and 216, the potentiometer 215 being used in full wave or AC operation and the potentiometer 216 being used in half wave operation. As shown, the potentiometer 215 is connected to the terminal 63 and the potentiometer 216 is connected to a terminal 218 which is not used in the system as illustrated but is available for use for half wave operation, if desired. Fixed resistors 219 and 220 are shown connected between the terminals 63 and 218 and the ground line 190, in parallel with the potentiometers 215 and 216.

To develop a voltage signal at circuit point 206, it is connected through a resistor 221, a diode 222 and a secondary winding 223 of a transformer 224 to the terminal which, as above noted, is supplied with a negative bias voltage relative to the ground line 190. The transformer 224 has a primary winding 225 connected at one end to the terminal 67 and at the other end through a resistor 226 to the terminal 68, an AC voltage proportional to the magnetizing voltage being applied to the terminals 67 and 68.

As shown, a terminal 227 is connected through an adjustable resistor 228 to the cathode of the diode 222. Terminal 227 is not used in the embodiment of FIG. 1 but is available for use in applying a DC voltage signal to the control circuit, which is desirable in certain arrangements, including the modification of FIG. 11 as hereinafter described.

With regard to the amplifier 207 used for switching from voltage to current control, it has a first input connected through a resistor 230 to the ground line 190 and also through a resistor 231 to the junction between resistor 221 and diode 222. A second input of the amplifier 207 is connected to its output through the parallel combination of a resistor 232, three diodes 233 in series and a capacitor 234. The second input of the amplifier 207 is connected through a resistor 236 to a circuit point 237 which is connected through a capacitor 238 and a diode 239 to ground and through a resistor 240 and two diodes 241 and 242 to the terminals 63 and 218 for application of AC or half wave current signals to the amplifier 207.

In the operation of the circuit, a voltage is initially applied for magnetization of a part. Before current starts to flow, the output of the circuit 60, at the terminal 62, is controllable by the feedback voltage signal which is applied between terminals 67 and 68 and which develops a voltage at the circuit point 206, applied through diode 205 to the input of the amplifier 192. The voltage then applied to the part may then be at a level high enough to break down any contact resistance between the part and the headstock 11 and the tailstock 12, thus tending to insure that current will start to flow. However, the voltage feedback signal serves to limit the applied output voltage which is desirable. A high starting voltage is not desirable especially when the type of part is such that a low current is selected. As the current starts to flow in the part, or in the magnetizing coil and after it reaches a certain level, a signal is developed at the cathode of the diode 241 which is applied through resistors 240 and 236 to the input of the amplifier 207. The output of amplifier 207 then goes to a low level, thereby clamping the potential of the circuit point 206 at a low level and precluding further control in response to the feedback voltage signal. Thereafter, the control is solely in response to a comparison between the load current signal and the reference signal which are respectively applied through the resistors 203 and 200 to the input of the amplifier 192.

To supply operating voltages for the amplifiers 204 and 207, and also to develop a bias voltage, a power supply circuit is provided including a transformer 244 having a primary winding 245 connected to the terminals 75 and 76 and a secondary winding 246 which has a center tap connected to the line 190 and end terminals connected through diodes 247 and 248 to lines 249 and 250 which are connected to the amplifiers 204 and 207. The line 250 is also connected through resistors 251 and 252 to circuit points which are connected to terminals 61 and 72, such circuit points being connected through zener diodes 253 and 254 to ground. In this way, a bias level is applied to the terminal 61.

It is also noted that filter capacitors 255 and 256 are connected between the lines 249 and 250 and the ground line 190.

The line 250 is also connected to a negative power supply input of the output amplifier 192. The positive power supply input of the amplifier 192 is connected through a protective diode 258 to ground and through a diode 259 to a terminal 260 which is connected to the terminal 181 of the power module 50, to receive operating power therefrom when the contact 185 is closed.

Figure 9:
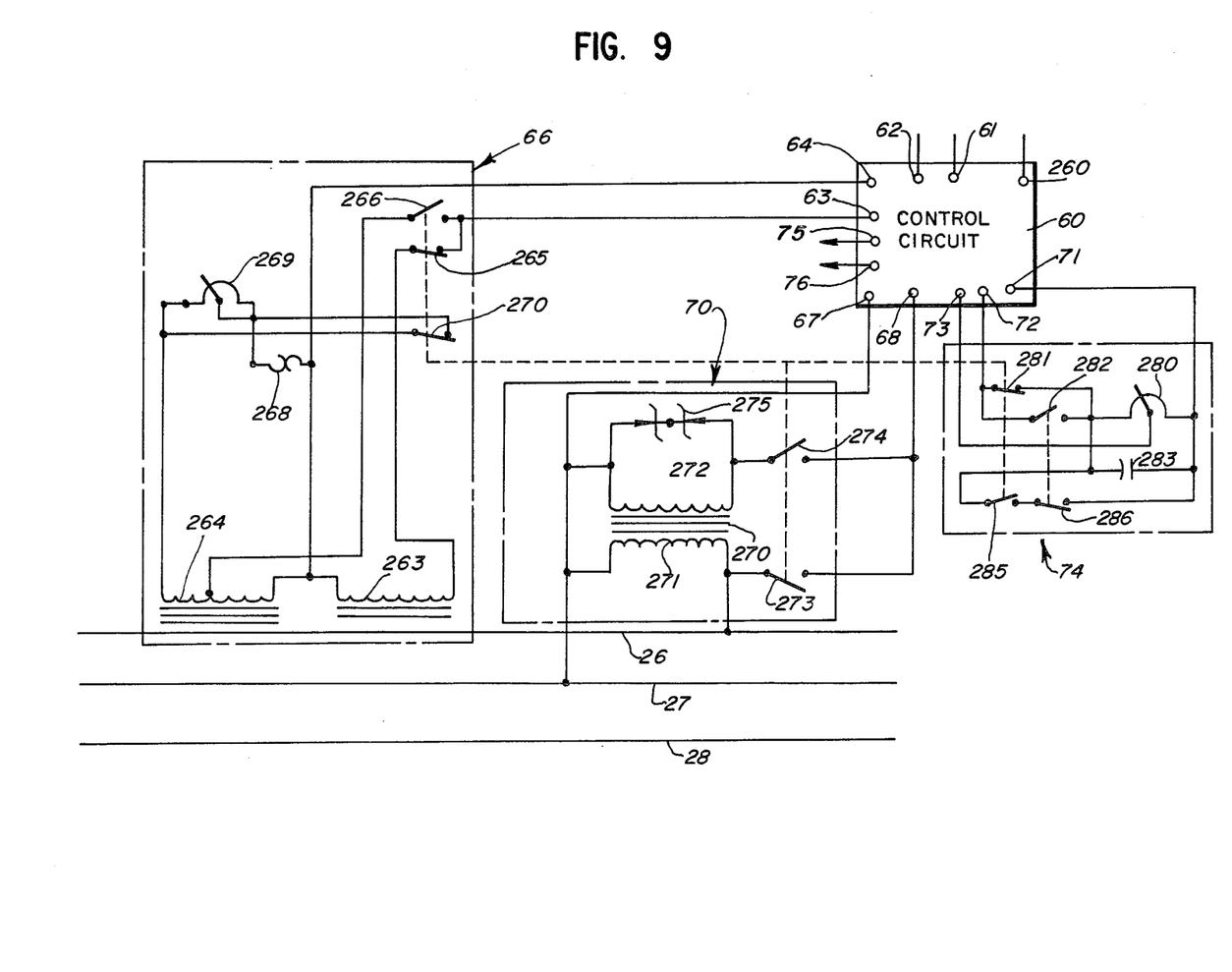
FIG. 9 is a circuit diagram illustrating a current transformer circuit, a voltage signal circuit and a regulator circuit of the system of FIG. 1, also showing the connections of such circuits to the control circuit of FIG. 8.

FIG. 9 shows the current transformer circuit 66 which includes windings 263 and 264 both inductively coupled to the line 26 between the transformer 36 and the rectifier 15. The winding 263 is connected at one end through a relay contact 265 to the terminal 63 of the control circuit 60 and at its opposite end to the terminal 64 of the control circuit 60. Except upon closure of a low current control switch, not shown, the contact 265 is closed and the control circuit 60 is then responsive to a signal developed by the winding 263.

When the low current control switch is closed, the contact 265 is opened and a contact 266 is closed to connect terminal 63 of the control circuit 60 to a tap of winding 264, one end of winding 264 being connected to terminal 64. The control circuit 60 is then controlled by the signal developed between the tap of winding 264 and the end thereof which is connected to terminal 64.

The winding 264 is also used for overload protection. A device 268 is connected between ends of the winding 264 and operates contacts in series with the coils of contactors (not shown) which control the contacts 17 and 18 which are connected to the headstock 11 and coil 13. A low current calibration potentiometer 269 is connected in series with the device 268 and in parallel with a contact 270 which is closed except during low current operation.

FIG. 9 also shows the voltage sensing circuit 70 which includes a transformer 270 having a primary winding 271 and a secondary winding 272. The lines 26 and 27 are connected to the primary winding 271 and also the line 26 is connected through a relay contact 273 to the terminals 68 and 67 of the control circuit 60, contact 273 being closed except during low current operation. During low current operation, the secondary winding 272 is connected through a relay contact 274 to the terminals 67 and 68, a higher voltage being then applied to the control circuit 60. By way of example, transformer 270 may have a 5:1 step-up ratio. A voltage limiting device 275 is connected across the secondary winding 272.

FIG. 9 also illustrates the components of the regulator circuit 74 which functions to apply a reference signal to terminal 73 of the control circuit 60 which is shown in FIG. 8 and which is described in detail above. Terminal 73 is connected to the movable contact of a potentiometer 280 which has one end terminal connected to the terminal 71 and an opposite end terminal connected to the terminal 72, either through a normally closed contact 281 of a low current control relay or through a normally open contact 282, of a magnetizing current control relay. A capacitor 283 is connected in parallel with the potentiometer 280. Also, a normally open contact 285 of the low current control relay and a normally closed contact 286 of the magnetizing current control relay are connected in series across the potentiometer 280. Thus a short circuit of the potentiometer 280 and the parallel capacitor 283 is provided whenever the low current control relay is energized to close the contact 285 and whenever at the same time the magnetizing current control relay is deenergized to keep the contact 286 in its normally closed condition. Terminals 71 and 72 are connected to the regulated voltage supply including the zener diode 254 within the control circuit 60, shown in FIG. 8 and described in detail above. The voltage supply which includes the zener diode 254 is operative to supply a regulated voltage. By way of example, the terminal 72 may be at minus 10 volts relative to the terminal 71.

Figure 10:
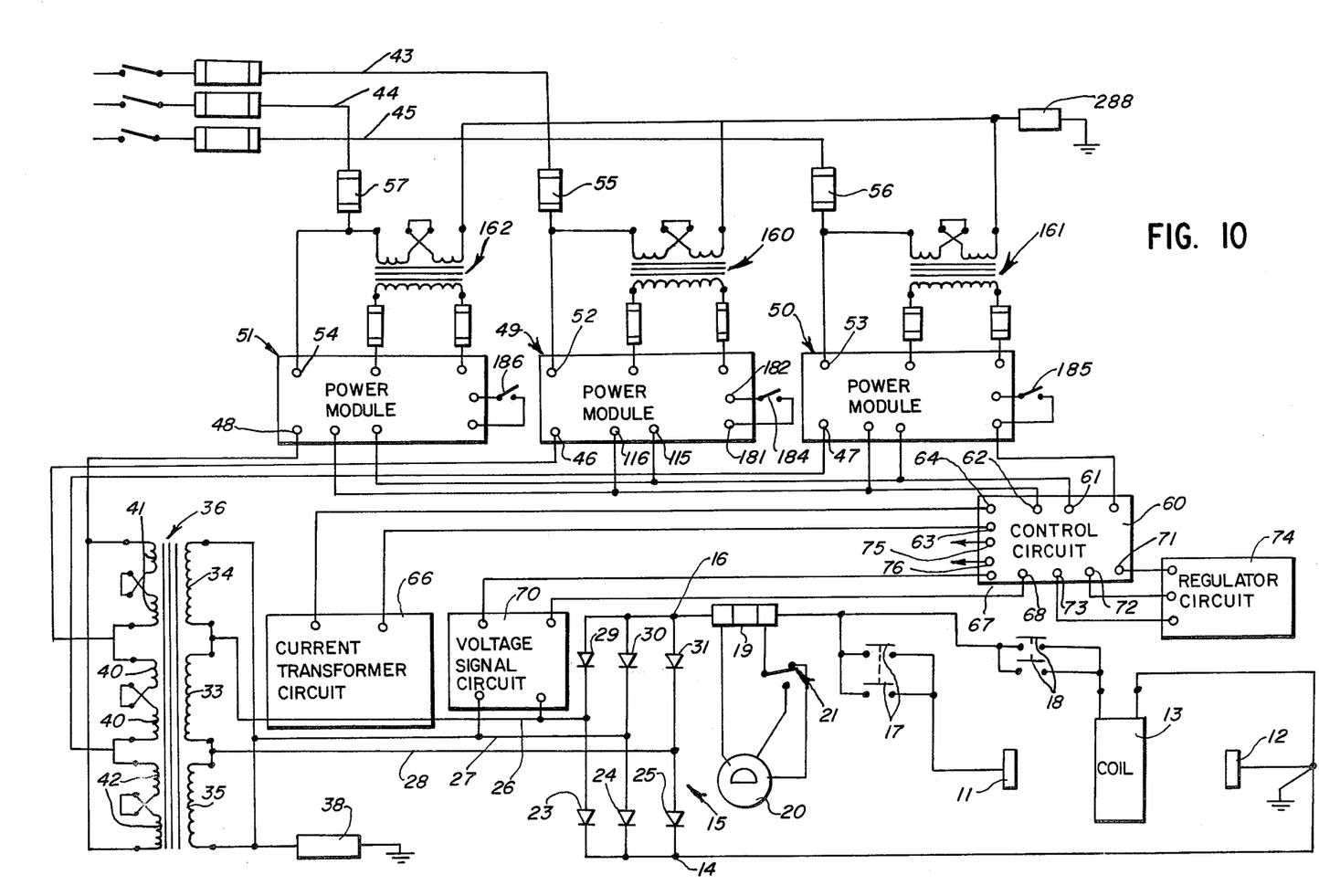
FIG. 10 is a schematic diagram of one modified system according to the invention.

FIG. 10 illustrates a modified system 10' in which direct interconnections are provided between primary windings 40, 41 and 42 of the transformer 36 to provide a delta configuration of connections thereof and in which the power modules 49, 50 and 51 are respectively connected in series between the supply lines or buses 43, 45 and 44 and the interconnections of the primary windings of the transformer 36. Thus the modules are outside a delta connection of the primary windings rather than within a delta connection of the primary windings as shown in FIG. 1. The primary windings of the transformers 160, 161 and 162 are respectively connected between the supply buses 43, 45 and 44 and a neutral point which may be connected through an impedance 288 to ground. The primary windings 40, 41 and 42, as shown in FIG. 10, are connected directly in a delta fashion, being connected, respectively, between lines 43 and 44, lines 44 and 45 and lines 45 and 43. If desired, a "Y" connection might be used in place of the illustrated delta connection.

Figure 11:
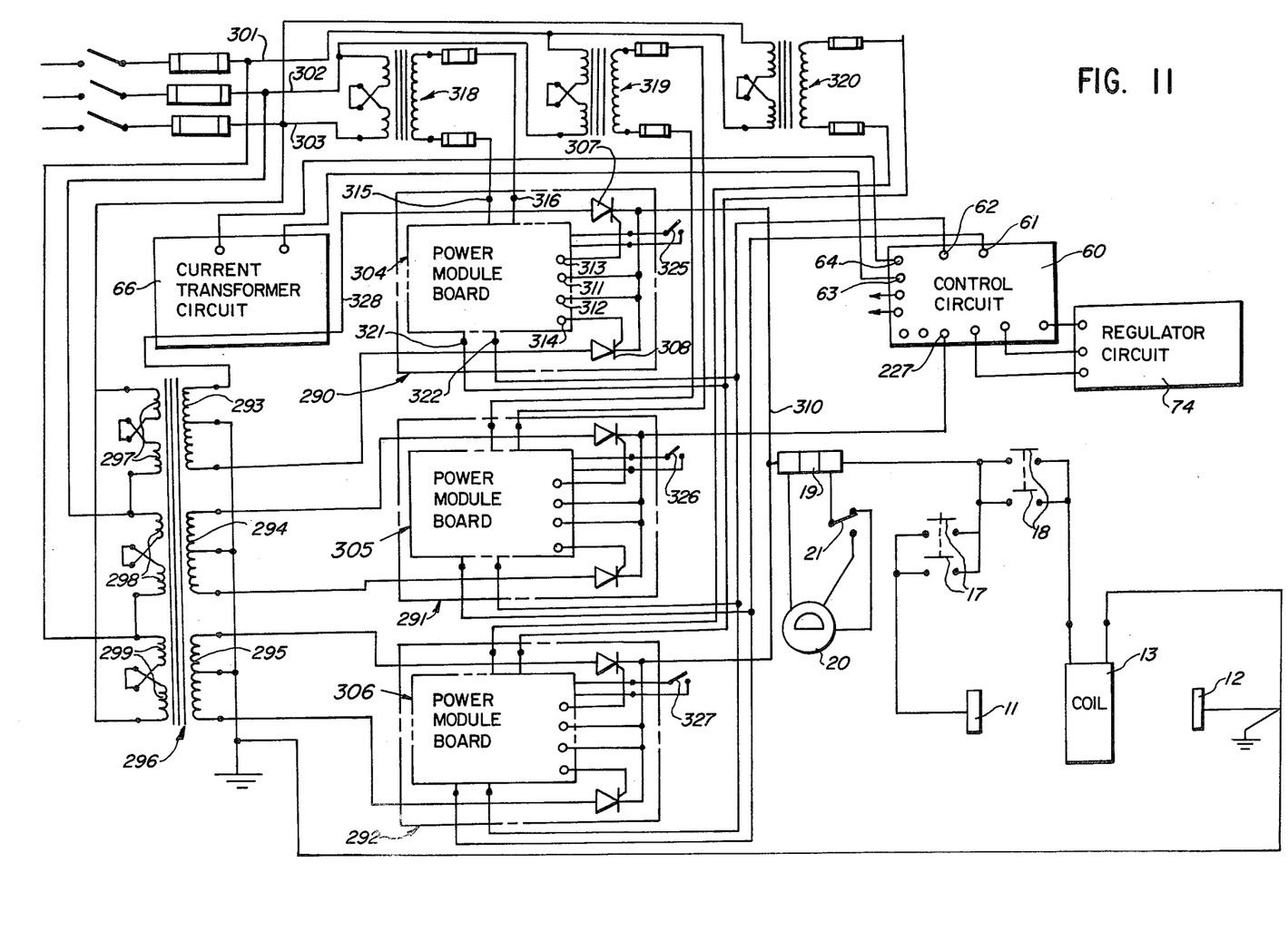
FIG. 11 is a schematic diagram of another modified system constructed in accordance with the principles of the invention.

FIG. 11 illustrates another modified arrangement in which power modules 290, 291 and 292 are connected between secondary windings 293, 294 and 295 of a three phase transformer 296 and magnetizing circuitry which is the same as shown in FIG. 1. The transformer 296 has three pairs of primary windings 297, 298 and 299, each pair being connected in series in the illustrated arrangement. As shown, the three pairs of primary windings are connected in delta fashion to the supply buses 301, 302 and 303 but a "Y" connection may be used, if desired.

The power modules 290, 291 and 292 include circuit boards 304, 305 and 306, each of which may have the same circuitry as the circuit board 84 as illustrated in FIG. 2. The power modules 290, 291 and 292, however, include silicon-controlled rectifiers connected in a manner somewhat different from the connections shown in FIG. 2. In particular, the power module 290 includes a pair of silicon-controlled rectifiers 307 and 308 which are connected between end terminals of the winding 293 and a line 310 connected to the magnetizing circuitry, a center tap of the winding 293 being connected to ground. The line 310 is connected to terminals 311 and 312 of the board 304 and the gate electrodes of the silicon-controlled rectifiers 307 and 308 are connected to terminals 313 and 314 of the board 304. The terminals 311, 312, 313 and 314 of the board 304 respectively correspond to the terminals 85, 86, 87 and 88 of the board 84 as illustrated in FIG. 2.

The power module 290 further includes terminals 315 and 316 to which a supply and phase control voltage is applied through a step-down transformer 318 connected to the supply buses 302 and 303. The other two power modules 291 and 292 are connected to the secondary windings 294 and 295 and have the same circuitry as the power module 290, supply and phase control voltages being applied thereto through transformers 319 and 320 respectively connected to buses 301 and 302 and buses 303 and 301.

The power module 290 also includes control input terminals 321 and 322 which are connected to similar terminals of power modules 291 and 292 and to terminals 61 and 62 of the control circuit 60. Operation of the modules 290, 291 and 292 is controlled by contacts 325, 326 and 327 of a relay operated by a pushbutton or foot switch, not shown.

The current transformer circuit 66 is used in the arrangement of FIG. 11 in the same way as in the embodiment of FIGS. 1, 2, 8 and 9, being operative to sense current in a line 328 in series with the rectifier 307 and having output terminals connected to terminals 63 and 64 of the control circuit 60. Also, the same regulator circuit 74 is used to control the control circuit 60 in the same way as in the embodiment of FIGS. 1, 2, 8 and 9.

In the arrangement of FIG. 11, the voltage signal circuit 70 is not used and, instead, a DC voltage is applied to the control circuit 60, the terminal 227 being connected to the line 310 and the terminal 61 being connected to ground so that a DC signal proportional to the magnetizing voltage is applied within the control circuit 60. With reference to FIG. 8, the DC signal is applied through adjustable resistor 228 and resistors 221 and 231 to the circuit point 206 and the operational amplifier 207, the voltage being applied with respect to a bias level established by the zener diode 253.

The arrangement of FIG. 11 has important advantages in that the rectification and control functions are combined in one unit. This simplifies manufacture, installation and servicing of the units. It also facilitates trouble shooting and servicing and it has important advantages from the standpoint of safety, since the power modules are isolated from the high voltage input.

It is also noted that in this arrangement in which the control of current is through the control of silicon-controlled rectifiers in the secondary circuit, the arrangement as shown using the center tapped secondary windings 293-295 is advantageous in that it simplifies the control operation and connections. In addition, it permits direct grounding of terminals of the secondary windings which is an important safety feature.

It is additionally found that with an arrangement as shown in FIG. 11, a more reliable quick break magnetizing operation can be obtained.

Other connection arrangements may be used but it is important in any case that connections and circuits equivalent to those illustrated be used with the same control signal being applied to all three modules and with the same relationship being obtained in all three modules between the magnitude of the control signal and the phase angle of firing of the SCR's. It is also important that reference phase points be accurately established, through circuitry equivalent to that shown in FIG. 2, operative through the transformers 160-162 from the input buses. With such circuitry as illustrated, a balanced operation of the three phases is obtained and the system is highly reliable.

It will be understood that modifications and variations may be made without departing from the spirit and scope of the novel concepts of this invention.

What is claimed is:

1. In a magnetic particle inspection system, magnetizing means for operation at high current and low voltage levels and arranged for association with a part to be inspected for applying a magnetizing field thereto, and a current supply for supplying a current of accurately controlled duration and magnitude to said magnetizing means to accurately control the duration and intensity of the magnetizing field applied to said part, said current supply comprising: first, second and third input lines for connection to a three-phase AC power supply, three-phase voltage step-down transformer means including first, second and third primary winding means and first, second and third secondary winding means, connection means arranged to provide substantially direct connections between said first, second and third input lines and said first, second and third primary winding means, first, second and third power modules respectively connected between said first, second and third secondary winding means and said magnetizing means, said first, second and third power modules respectively including first, second and third silicon-controlled rectifier means, each arranged for conducting a high level of current of one phase and of one polarity from the associated one of said secondary winding means and to said magnetizing means, first, second and third firing means for respectively controlling triggering of said first, second and third silicon-controlled rectifier means, first, second and third phase angle control means for respectively controlling the time of operation of said first, second and third firing means in each cycle, and a control circuit arranged to control said first, second and third firing means and said first, second and third phase angle control means to control the time of initiation and termination of current flow to said magnetizing means and to control the phase angle of firing of said silicon-controlled rectifier means, to thereby apply a magnetizing field of accurately controlled duration and intensity to said part, said silicon-controlled rectifier means and the associated circuitry of said power modules being substantially isolated by said transformer means from any voltage transients developed by said three-phase AC power supply.

2. In a system as defined in claim 1, current sensing means for developing a current signal proportional to the current applied to said magnetizing means, and means in said control circuit for responding to said current signal to simultaneously control said first, second and third phase angle control means and to maintain said magnetizing current at an optimum value during magnetization of a part.

3. In a system as defined in claim 2, regulating means for supplying an adjustable reference signal, said control circuit including means for comparing said current signal with said reference signal for simultaneously controlling all three of said first, second and third phase angle control means to maintain magnetizing current at a value corresponding to the magnitude of said adjustable reference signal.

4. In a system as defined in claim 2, voltage sensing means for developing a voltage signal proportional to the voltage applied to said magnetizing means, said control circuit including means responsive to said voltage signal for modifying the simultaneous control of said first, second and third phase angle control means in accordance therewith.

5. In a system as defined in claim 4, said control circuit being operative to control said phase angle control means independently of said voltage signal after said current signal reaches a certain level.

6. In a system as defined in claim 1, manually controllable contact means having first and second positions, said control circuit being responsive to operation of said contact means to said first position for initiating conduction of said silicon-controlled rectifier means in the cycle immediately following operation of said contact means to said first position, and said control means being responsive to operation of said contact means to said second position to terminate conduction of said silicon-controlled rectifier means in the cycle immediately following operation of said contact means to said second position.

7. In a system as defined in claim 1, each of said first, second and third secondary winding means comprising a secondary winding having end terminals and having a center tap, means connecting said center taps together and to one input terminal of said magnetizing means, each of said first, second and third silicon-controlled rectifier means comprising a pair of silicon-controlled rectifiers connected between said end terminals of the corresponding one of said secondary windings and the other input terminal of said magnetizing means, each of said pairs of silicon-controlled rectifier being so poled as to conduct in 180 degree phase relation.

8. In a system as defined in claim 7, means connecting said center taps and said one input terminal of said magnetizing means to a common ground.

9. In a system as defined in claim 1, each of said phase angle control means comprising a controllable timing circuit arranged to be triggered at the beginning of a half cycle of one phase of the voltage applied from said three-phase AC power supply and arranged to be controlled from said control current to control the time of operation of said firing means and to trigger the associated silicon-controlled rectifier means at a phase angle variable from a time near the beginning of said half cycle to a time near the end of said half cycle.

10. In a system as defined in claim 9, each of said firing means comprising means for developing and applying to said silicon-controlled rectifier means a series of pulses at a frequency substantially higher than the frequency of the three-phase voltage applied from said three-phase AC power supply.

11. In a system as defined in claim 9, each of said first, second and third secondary winding means comprising a secondary winding having end terminals and having a center tap, means connecting said center taps together and to one input terminal of said magnetizing means, each of said first, second and third silicon-controlled rectifier means comprising a pair of silicon-controlled rectifiers connected between said end terminals of the corresponding one of said secondary windings and the other input terminal of said magnetizing means, each of said pairs of silicon-controlled rectifier being so poled as to conduct in 180 degree phase relation and each of said phase control means comprising a pair of said ramp circuits.

12. In a system as defined in claim 11, manually controllable contact means having first and second positions, said control circuit being responsive to operation of said contact means to said first position for initiating conduction of said silicon-controlled rectifier means in the cycle immediately following operation of said contact means to said first position, and said control means being responsive to operation of said contact means to said second position to terminate conduction of said silicon-controlled rectifier means in the cycle immediately following operation of said contact means to said second position.

* * * * *